(12) United States Patent
Shealy et al.

(10) Patent No.: US 10,967,194 B2
(45) Date of Patent: Apr. 6, 2021

(54) PULSED ELECTROMAGNETIC FIELD DEVICE AND METHODS OF USE

(71) Applicant: Shealy-Sorin Wellness, LLC, Fair Grove, MO (US)

(72) Inventors: C. Norman Shealy, Fair Grove, MO (US); Sergey Sorin, Springfield, MO (US); Francis L. Cassady, Edwardsville, IL (US)

(*) Notice: Subject to any disclaimer, the term of this patent is extended or adjusted under 35 U.S.C. 154(b) by 0 days.

(21) Appl. No.: 16/401,414

(22) Filed: May 2, 2019

(65) Prior Publication Data

US 2019/0336782 A1    Nov. 7, 2019

Related U.S. Application Data

(60) Provisional application No. 62/665,827, filed on May 2, 2018.

(51) Int. Cl.
*A61N 2/02*      (2006.01)

(52) U.S. Cl.
CPC ..................................... *A61N 2/02* (2013.01)

(58) Field of Classification Search
CPC A61N 2/02; A61N 2/00–12; A61M 21/00–02
See application file for complete search history.

(56) References Cited

U.S. PATENT DOCUMENTS

| | | |
|---|---|---|
| 3,658,051 A | 4/1972 | MacLean |
| 3,915,151 A | 10/1975 | Kraus |
| 4,266,532 A | 5/1981 | Ryaby et al. |
| 4,527,550 A | 7/1985 | Ruggera et al. |
| 5,014,699 A | 5/1991 | Pollack et al. |
| 5,030,196 A | 7/1991 | Inoue |
| 5,160,591 A | 11/1992 | Liboff et al. |
| 5,269,745 A | 12/1993 | Liboff et al. |
| 5,269,746 A | 12/1993 | Jacobson |
| 5,437,600 A | 8/1995 | Liboff et al. |
| 5,518,495 A | 5/1996 | Kolt |
| 5,620,463 A | 4/1997 | Drolet |
| 5,752,911 A | 5/1998 | Canedo et al. |
| 6,083,149 A | 7/2000 | Wascher et al. |
| 6,149,577 A | 11/2000 | Bouldin et al. |
| 6,200,259 B1 | 3/2001 | March |
| 6,261,831 B1 | 7/2001 | Agee |
| 6,349,233 B1 | 2/2002 | Adams |
| 6,443,882 B1 | 9/2002 | Wascher et al. |
| 6,675,047 B1 | 1/2004 | Konoplev et al. |
| 2002/0103411 A1 | 8/2002 | Bailey et al. |

(Continued)

FOREIGN PATENT DOCUMENTS

| | | |
|---|---|---|
| EP | 0048451 A1 | 3/1982 |
| WO | 200115770 A2 | 3/2001 |

*Primary Examiner* — Thaddeus B Cox
(74) *Attorney, Agent, or Firm* — Tiffany C. Miller; Inventions International Inc.

(57) ABSTRACT

A device for generating pulsed electromagnetic fields is described, along with methods of using the device to treat patients by exposure to the pulsed electromagnetic fields. The treatments utilize pulsed electromagnetic fields based on the fundamental Schumann resonance frequency and the first 6 harmonics of that frequency. Various embodiments of the treatment methods include frequency sweeps across or hops between one or more of the Schumann resonance frequencies.

18 Claims, 7 Drawing Sheets

(56) References Cited

U.S. PATENT DOCUMENTS

| | | |
|---|---|---|
| 2002/0151759 A1 | 10/2002 | Paturu |
| 2002/0169355 A1 | 11/2002 | Rohan et al. |
| 2003/0130709 A1 | 7/2003 | D.C. et al. |
| 2005/0101827 A1 | 5/2005 | Delisle |
| 2005/0171397 A1* | 8/2005 | Baugh .................... A61N 2/02 600/14 |
| 2005/0182287 A1* | 8/2005 | Becker .................. A61N 2/008 600/13 |
| 2006/0241333 A1 | 10/2006 | Hunter |
| 2007/0078292 A1 | 4/2007 | Markov et al. |
| 2008/0097142 A1* | 4/2008 | Savage .................... A61N 2/02 600/14 |
| 2010/0113862 A1 | 5/2010 | Kotowich et al. |
| 2011/0105827 A1* | 5/2011 | Hesse .................. A61F 5/0003 600/14 |
| 2013/0137918 A1* | 5/2013 | Phillips .................... A61N 2/02 600/14 |
| 2017/0072210 A1* | 3/2017 | Gangwish ................ A61N 7/00 |

\* cited by examiner

PULSED ELECTROMAGNETIC FIELD DEVICE AND METHODS OF USE

CROSS-REFERENCE TO RELATED APPLICATIONS

This application claims the benefit of U.S. Patent Application Ser. No. 62/665,827 filed May 2, 2018, the disclosure of which is incorporated herein by reference.

BACKGROUND

The human nervous system coordinates the functioning of the body and its detection and response to environmental stimulae. The rapid transmission of electrical signals is one of the basic functions of the nervous system. By their nature, electrical signals interact with, may generate, and are generated by magnetic fields. Thus magnetic fields may be used to induced desired effects on the nervous system of a human patient.

The components of the nervous system may be altered or stimulated by the presence of electromagnetic fields. In some cases such exposure may lead to damage to the nervous system. In other cases, the exposure may have beneficial effects on the nervous system and body of the human exposed to the fields.

Pulsed Electromagnetic Fields (PEMF) are electromagnetic fields that vary over time. Natural phenomena such as lightning bolts may generate PEMF. These naturally-occurring PEMF create a global electromagnetic resonance within the electromagnetic field of the earth. These resonances arise due to the waveguide characteristics of the Earth's ionosphere. These resonances are called Schumann resonances after the physicist who discovered their existence.

The fundamental Schumann resonance has a frequency of 7.83 Hz, with additional harmonics of the fundamental resonance occurring at higher order resonance frequencies of the ionosphere. The additional harmonics may occur at multiples of the fundamental frequency up to or above the seventh order harmonic. Alternative calculations have located the additional harmonics at about 6.5 Hz intervals above the fundamental mode at 7.83 Hz.

Humans evolved on the planet in the presence of these Schumann resonances. The seven lowest frequency Schumann resonance frequencies are also believed to correspond to each of the seven Chakra's of the human body, and application of PEMF in the corresponding frequency on the Chakra's may have numerous beneficial effects.

SUMMARY OF THE INVENTION

A device is described for using a coil of wire to generate a PEMF in proximity to a patient's body. In some embodiments, the device includes a control unit to generate specific frequencies of PEMF in specific desired ranges and for desired time periods and variable steps between PEMF frequencies.

Methods described herein of treating patients by applying pulsed electromagnetic fields (PEMF) to certain portions of the patient's body have beneficial impacts on the health of the patient. The methods include various frequency sweeps and frequency hopping protocols for treatment of a patient.

In various embodiments, the invention consists of a method of treating a patient with a pulsed electromagnetic field generated using a conductive coil. This embodiment of the inventive method includes the steps of positioning the conductive coil on a body part of the patient; energizing the conductive coil with an oscillating electrical current sufficient to generate a pulsed electromagnetic field that impinges on the body part of the patient; wherein the oscillating electrical current oscillates at a frequency in the Gamma frequency band. In some of these embodiments, the frequency of the oscillating electrical current is a target frequency selected from the Schumann harmonic resonance frequencies. In other embodiments, the frequency of the oscillating electrical current is selected from 7.83 Hz, 15.66 Hz, 23.49 Hz, 31.32 Hz, 39.15 Hz, 46.98 Hz, and 54.81 Hz.

In other versions of the inventive method, energizing the conductive coil consists of periodically and sequentially varying the frequency of the oscillating electrical current to more than one target frequency selected from the Schumann harmonic resonance frequencies. This may be referred to as frequency hopping embodiments of the inventive method.

In some of these versions, the method includes incrementally varying the frequency of the oscillating electrical current in a range above and below each target frequency selected from the Schumann harmonic resonance frequencies. In some embodiments, the range may extend from 3 Hz lower than the target frequency to 4 Hz higher than the target frequency. In some versions of the method, the frequency is incrementally varied by 0.5 Hz or 1 Hz. In some versions of the method, the frequency is incrementally varied every 15 seconds.

In other methods, referred to as frequency sweeping, energizing the conductive coil consists of incrementally varying the frequency of the oscillating electrical current from a start frequency that is lower than the target frequency to an end frequency that is higher than the target frequency. In some versions, the start frequency is 3 Hz lower than the target frequency and the end frequency is 4 Hz higher than the target frequency. In some other versions of the method, it further consists of incrementally varying the frequency for a second target frequency selected from the Schumann harmonic resonance frequencies. In some embodiments, the method includes sequentially repeating the incrementally varying of the frequency for each target frequency in the Schumann harmonic resonance frequencies. In some versions of the method, the frequency is incrementally varied by 1 Hz every 15 seconds.

In an additional frequency sweep version of the inventive method, incrementally varying the frequency of the oscillating electrical current starts from a first frequency 2 Hz lower than the fundamental Schumann harmonic resonance frequency and ends at a second frequency 2 Hz higher than the seventh order Schumann harmonic resonance frequency. In some versions of this method, once the above sweep ends it reverses direction by incrementally varying the frequency of the oscillating electrical current from the second frequency back to the first frequency.

In other versions of the method, the frequency of the oscillating electrical current may be selected from the Schumann harmonic resonance frequencies and the Geomagnetic harmonic resonance frequencies.

The inventive method may be applied to any part of the human body, but in some specific embodiments the body part of the patient is selected from the group consisting of head, chest, neck, back, abdomen, wrist, hand, arm, elbow, shoulder, leg, knee, ankle, foot, and buttocks. In some versions of the method, positioning the conductive coil in relationship to a body part of the patient comprises placing the conductive coil adjacent to the head of the patient in a "halo" position.

In yet other versions of the method, positioning the conductive coil in relationship to a body part of the patient consists of positioning the patient in a supine posture, and placing the conductive coil on the chest or abdomen of the patient. In similar versions of the method, positioning the conductive coil in relationship to a body part of the patient consists of placing an arm or a leg of the patient through the conductive coil, and positioning the conductive coil around a treatment area of the arm or the leg selected from the group consisting of the shoulder, the upper arm, the elbow, the forearm, the wrist, the hand, the thigh, the knee, the calf, the ankle, and the foot. In yet other versions of the method, positioning the conductive coil in relationship to a body part of a patient consists of positioning the patient in a prone position, and placing the conductive coil on the back or buttocks of the patient.

DETAILED DESCRIPTION

Figure 1:
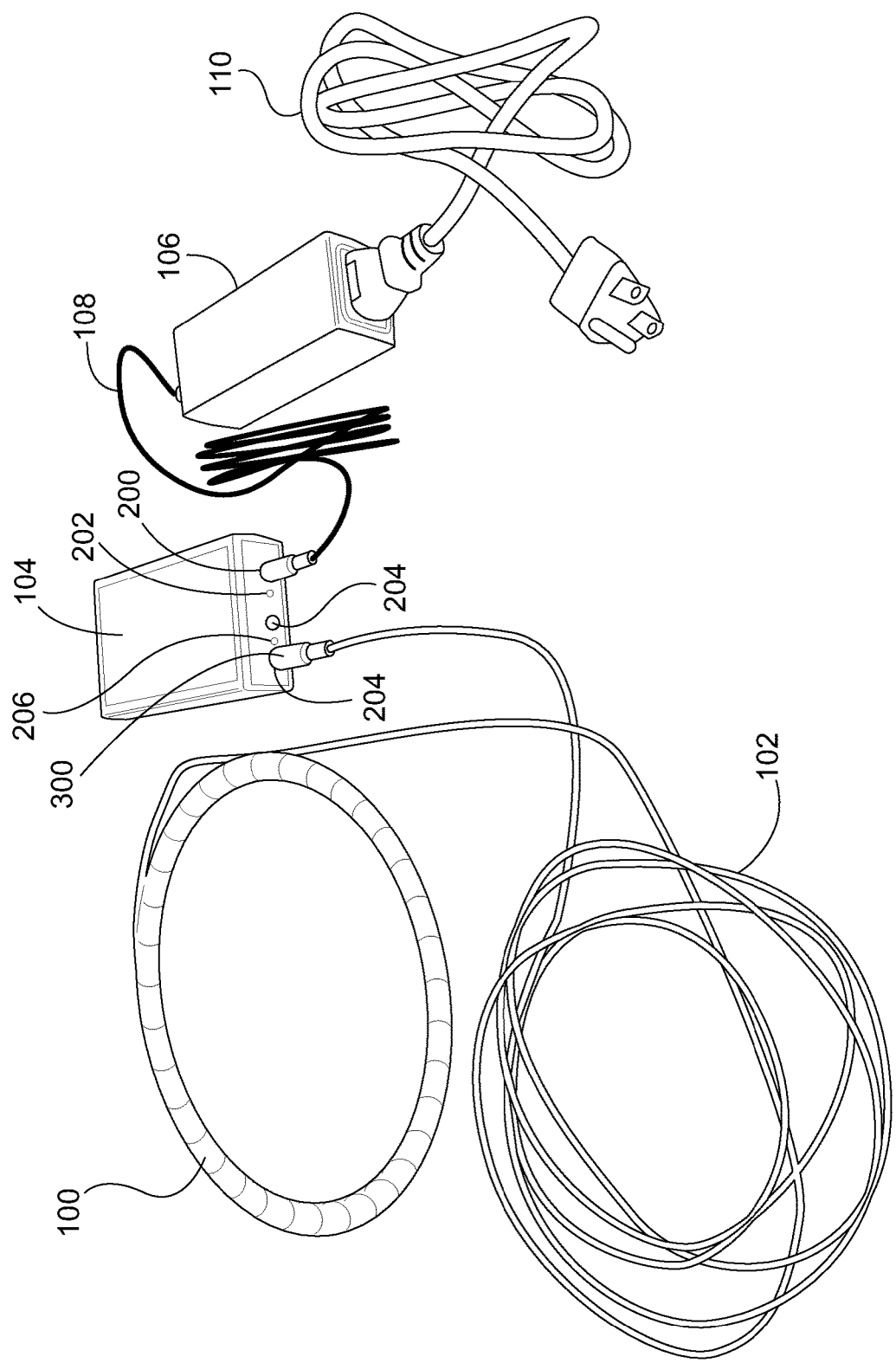
FIG. 1 is a perspective drawing of an embodiment of the PEMF device.

Application of PEMF to the human body may provide benefits of various kinds. Various methods of generating and applying PEMF may be beneficial. PEMF therapy comprises the targeted use of PEMF via its application to the body to produce beneficial effects or to treat maladies of various kinds. The use of intentionally created PEMF within the same frequency range as the natural PEMFd may heighten or intensify the beneficial effects of PEMF. Applying the PEMF in certain inventive patterns and to certain areas of the body may have beneficial effects.

It is believed that PEMF provides many benefits to the human body, such as:
1. recharging the TMP;
2. increasing ATP production in the mitochondria;
3. enhancing the sodium-potassium pump;
4. increasing cellular pH to make the cells and body more alkaline;
5. improving oxygen uptake and assimilation into the cells;
6. lowering blood viscosity and improving circulation and microcirculation;
7. creating a healthy level of electroporation (openings in the cells for improved nutrient transport and waste elimination).

As an example of the mechanism behind such beneficial effects, PEMF are believed to stimulate and interact with the human body on a cellular level. Inside each of the cells in a human body are 200 to 300 mitochondria. These mitochondria convert chemical energy from food into electrical energy, in the form of electrons in a high-energy state, and store them in Adenosine Triphosphate (ATP) molecules. The average person expends their body weight in ATP every day; since the normal person only has 50 grams of total ATP in their body, the ATP is recycled or recharged 1000 to 1500 times a day in the mitochondria. ATP is a rechargeable battery for energy in the human body.

The high-energy electrons stored in ATP fuel the living processes of the human body such as the immune, reproductive, respiratory, locomotive, healing, organ function, assimilation, circulation, and other systems in the body. It is believed that PEMF therapy can increase ATP synthesis in the mitochondria and energize the cellular pump or Transmembrane Potential (TMP). The cellular pump assists in maintaining a healthy cellular voltage or TMP and drives the absorption and assimilation of essential nutrients and the removal of metabolic waste, heavy metals, chemicals, free radicals, etc. Over 50% of the ATP produced fuels this cellular pump. PEMF therapy can assist in charging the cell's TMP so that ATP can be conserved for increased energy, healing, repair and other cellular functions.

The benefits of PEMF therapy may be increased by using it in a method that includes the Schumann resonance frequencies. As described herein, certain inventive treatment protocols based on selection and timing of PEMF therapy frequency are useful for treatment of maladies and for overall beneficial application.

It is also believed that PEMF therapy using these inventive methods may provide additional benefits beyond those received from the natural PEMF of the earth's magnetic field, including:
1. stronger bones;
2. Increased levels of endorphins and associated pain relief;
3. better sleep and human growth hormone secretion;
4. increased amounts of ATP;
5. improved oxygenation and circulation;
6. improved immune function;
7. relaxation and stress reduction;
8. nerve and tissue regeneration.

The additional benefit of the inventive methods described herein may arise from the relative strength of the fields generated by natural and therapeutic PEMF, from the ability to target the application of the therapeutic PEMF to specific areas of the human body, or from other unknown underlying causes.

Embodiments of a Device for PEMF Therapy

Referring now to FIG. 1, an embodiment of a device for generating and applying the PEMF to a patient is depicted. The device includes a coil 100 formed from a length of electrically conductive wire coiled into a loop. The single loop 100 shown in the figure may contain multiple loops of the same conductor to increase the magnetic field produced by the coil. In some embodiments the conductive wire is a metal wire, such as copper or aluminum, coated with a thin layer of insulation. In various embodiments, the insulation may be a layer of a polymer, enamel, or other durable, insulating material that is capable of being applied in layers of a desired thickness. This wire is sometimes referred to as magnet wire or enameled wire, and is typically used in applications requiring a coil of conductive wire, such as transformers, electromagnets, and similar applications.

An electrical current passing through coil 100 generates a magnetic field that is dependent on the shape and size of the coil 100, as well as the number of conducting loops in the coil 100. The size and shape of the coil 100 may vary. The depicted embodiment is substantially circular, but in other embodiments the coil 100 may be oval or of other shape. The size of the coil 100 may vary depending on the intended use of the coil. In embodiments designed to be used in proximity with the head of a patient, a circular coil 100 having a diameter of from 7 to 9 inches may be utilized. Coils of other sizes may be used in proximity to the wrists, elbows, ankles, knees, and other joints of a patient. These other coils 100 may be circular or oval, with diameters or major axes, respectively, of 3-9 inches.

Figure 5A:
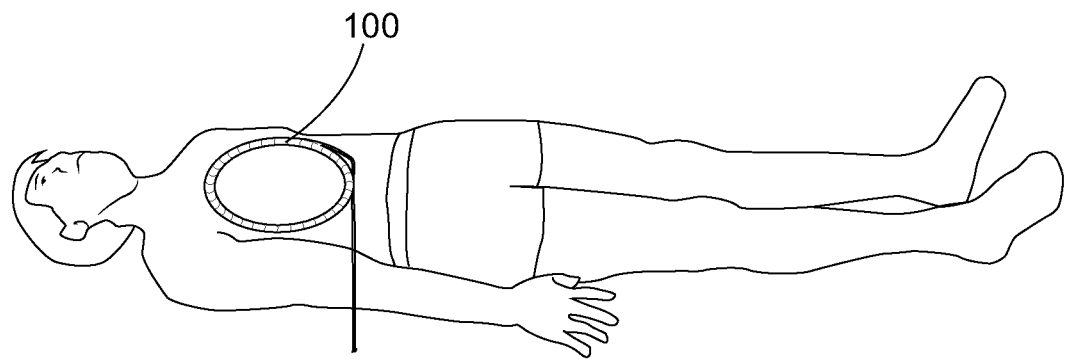
FIG. 5A is a depiction of an embodiment of the PEMF device in use to treat a patient.
Figure 5B:
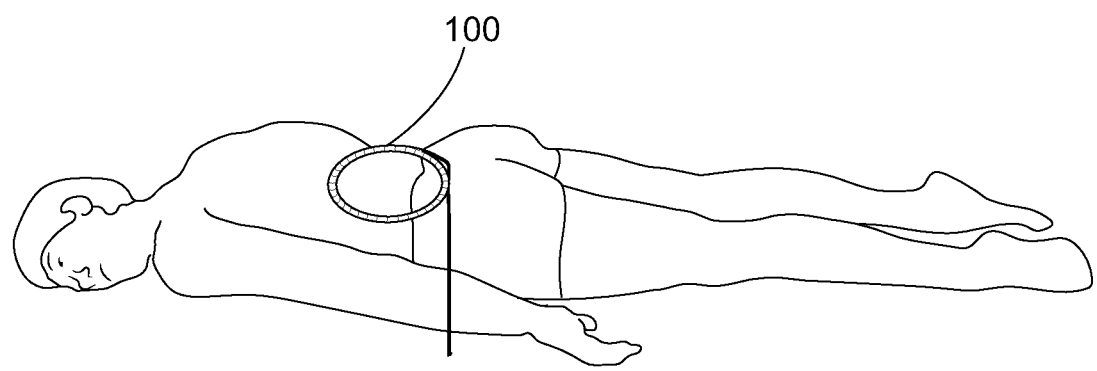
FIG. 5B is a depiction of an embodiment of the PEMF device in use to treat a patient.
Figure 5D:
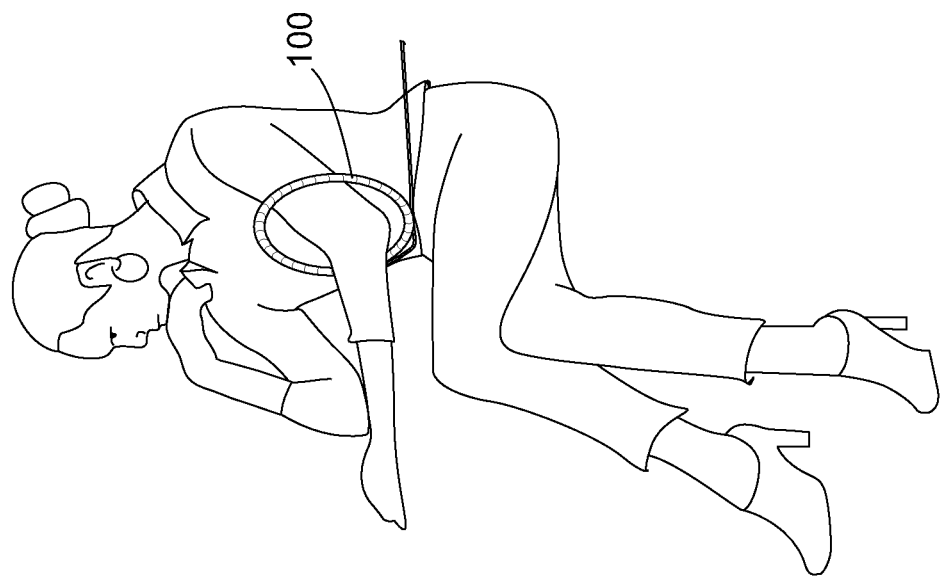
FIG. 5D is a depiction of an embodiment of the PEMF device in use to treat a patient.
Figure 5C:
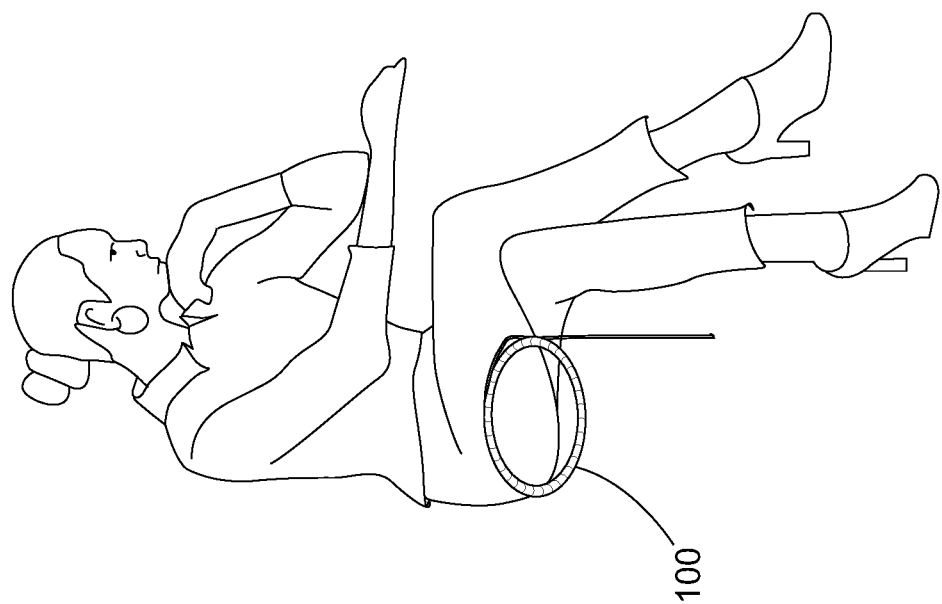
FIG. 5C is a depiction of an embodiment of the PEMF device in use to treat a patient.
Figure 5F:
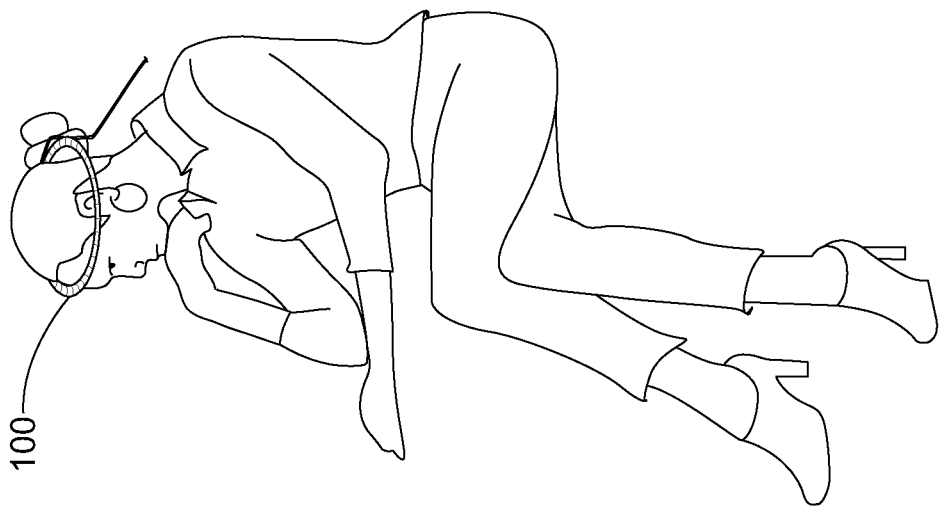
FIG. 5F is a depiction of an embodiment of the PEMF device in use to treat a patient.
Figure 5E:
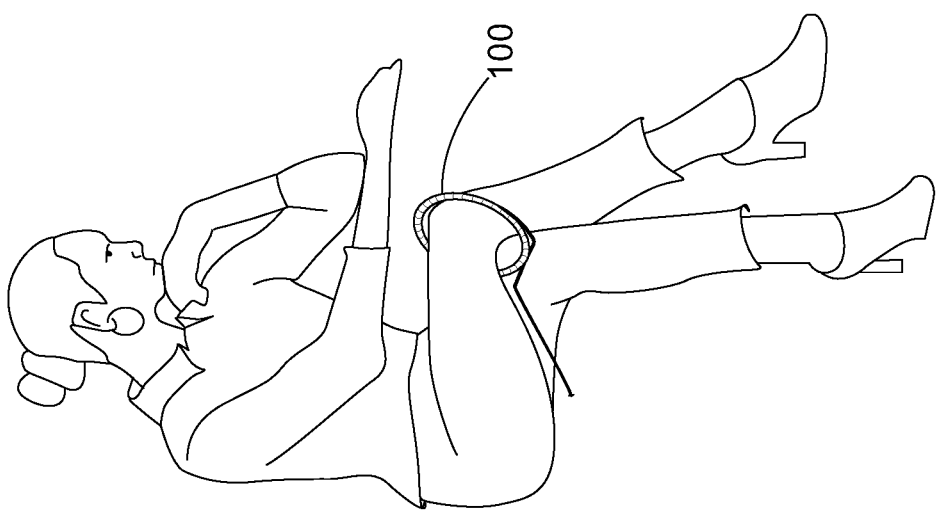
FIG. 5E is a depiction of an embodiment of the PEMF device in use to treat a patient.

In one method of treatment, the coil is placed above the top of a patient's head in a "halo" position as shown in FIG. 5F. The application of PEMF to the patient in this manner is believed to induce changes to the brain waves of the patient, such as inducing increased amplitude of neural oscillations in the gamma frequency band of approximately 30 Hz-150 Hz. This treatment is efficacious for the treatment of addiction disorders such as narcotics addiction.

Each end of the wire used to form the coil is electrically connected to a electrical power cord 102 having two insulated conductors. The power cord 102 provides electrical current to the coil 100 from a control unit 104. A conductive connector 300 having two electrical connections is provided on an end of power cord 102 for connecting the two conductors in cord 102 to the electrical circuitry provided in control unit 104. In some embodiments, the connector 300 may be a barrel type connector having an outer conductor and an inner conductor that are insulated from one another. The specific type of connector 300 that is used is not limiting of the device, and any known electrical conductor will serve the purpose. In some embodiments, two connectors 300 may be used, one for each conductor in the cord 102.

The control unit 104 is provided with one or more ports 204 for receiving connector 300 and creating an electrical connection between the coil and the circuitry in control unit 104. A control unit 104 may be provided with one or more port 204 to allow the control unit 104 to simultaneously drive more than one coil 100.

The control unit 104 is also provided with a power port 200 for receiving electrical power from a wall outlet or battery in a sufficient wattage and voltage to operate the electrical circuitry disposed in the control unit 104 and providing power to coil 100. The control unit 104 may also be provided with indicator lights 202 and 206 for indicating that the control unit 104 is supplied with the appropriate power, and that the electrical circuitry is operating property to cause the coil 100 to generate the desired PEMF.

In some embodiments, if the device receives power from a standard 120 volt 60 Hz a/c power source, a transformer 106 may be necessary to transform that electrical power to a desired input voltage and current for the control unit, via power cord 108. In some embodiments, the transformer 106 outputs 18 volt 1A d/c electrical power. In other embodiments of the device, the electrical circuitry may require different parameters for the input power supply.

Figure 2:
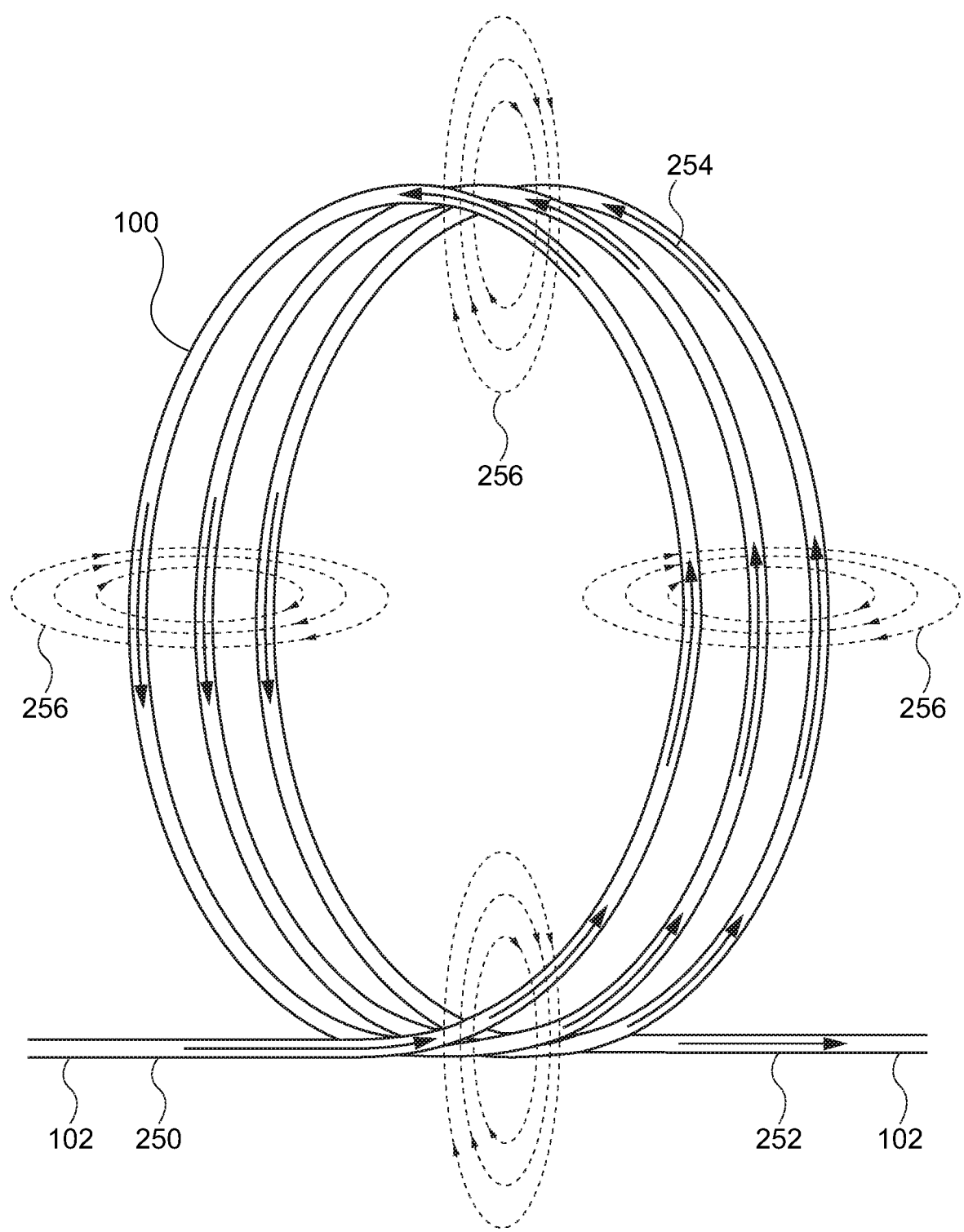
FIG. 2 is a schematic drawing of the current and magnetic fields generated by the coil used in embodiments of the PEMF device.

Referring now to FIG. 2, a schematic view of the magnetic field created by an embodiment of the device is depicted. The coil 100 includes one or more loops created in a conductor extending from a first end 250 of the coil 100 to a second end 252 of the coil 100. The first end 250 and second end 252 of the coil 100 are electrically connected via cord 102 to the connector 300 for electrical connection to the control unit 104. When an electrical current 254 runs through a looped conductor such as coil 100, a magnetic field 256 is generated by the current. If the current 254 varies in magnitude or direction, the magnetic field 256 will likewise vary in magnitude or direction, accordingly. In varying embodiments of the inventive device described herein, the electrical current 254 is an alternating current oscillating at the described frequencies, thus generating an alternating magnetic field 256 of the same frequency. In various embodiments, the electrical current 254 may have waveforms such a sinusoidal wave form, square wave form, triangle wave form, or sawtooth wave form, among others. The various loops in the coil 100 are disposed closely enough together so that the magnetic field generated by the current in the loops overlaps to create a stronger magnetic field then each loop would produce on its own.

Figure 3:
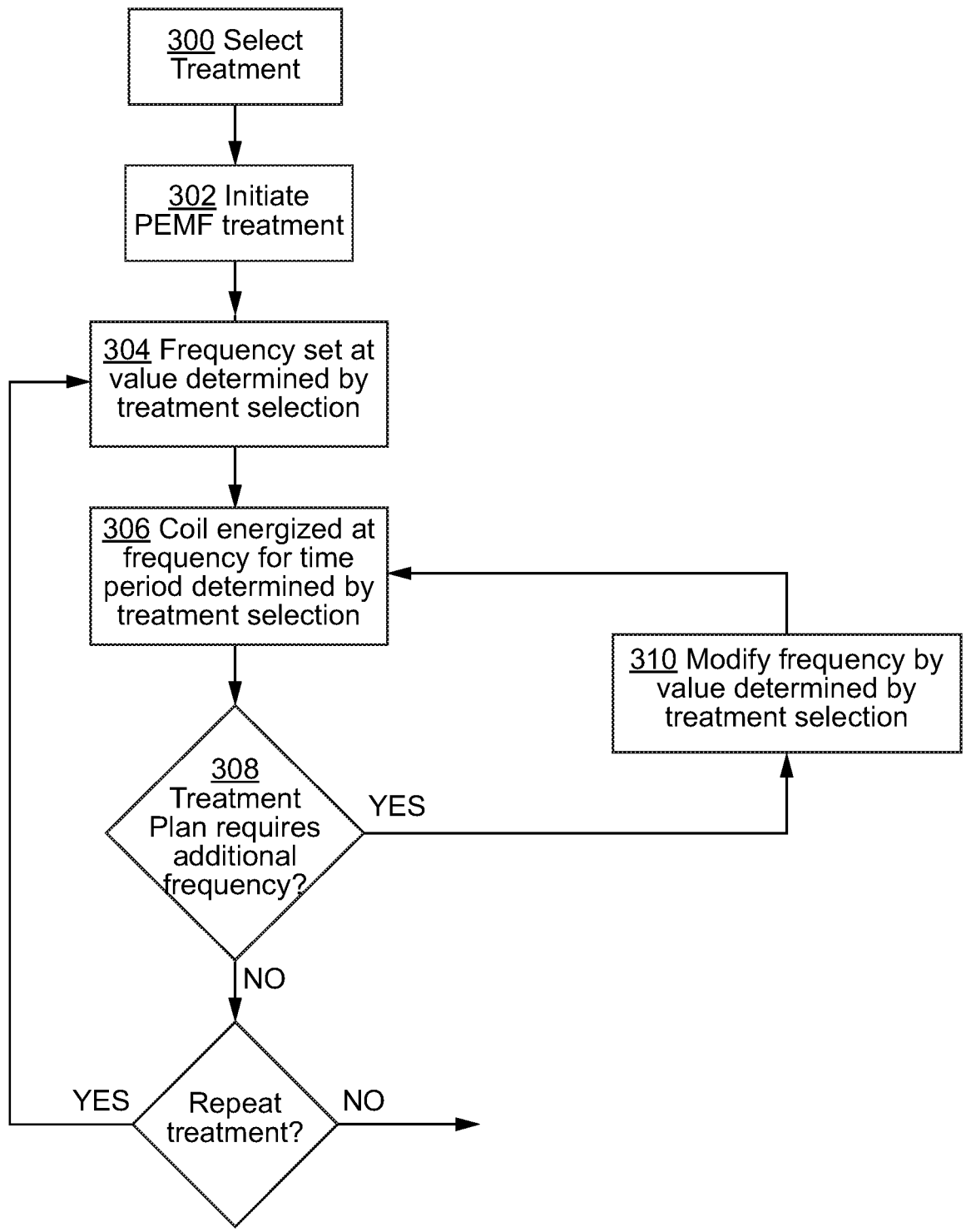
FIG. 3 is a schematic depiction of an embodiment of a method of using the PEMF device.

During use of various embodiments of the device, the electrical current may be at a set frequency or move between different frequencies for varying periods of time. Referring now to FIG. 3, a method of using an embodiment of the device is depicted in schematic form.

At step 300 a user selects a treatment protocol for use with the device. In varying embodiments, the process of selection may comprise setting switches or buttons on control unit 104, selecting options in a computer interface or via a wireless device, or other methods of configuring a device with settings of a desired value. These methods or functions may change over time, but one of skill in the art in designing medical or consumer devices will be able to adapt new such input methods or functions to embodiments of the device. Several specific embodiments of treatment methods that a user may select are described in more detail below.

Once the user has selected a treatment method or protocol, the PEMF treatment is initiated at step 302. During this step, the user places the coil 100 in position near, on, or around some part of the subject patient's body so that when electromagnetic fields 256 are generated by an electrical current 254 running through coil 100, those fields 256 will impinge upon or pass through a desired part of the subject's body.

During treatment, the control unit 104 follows the treatment method or protocol selected at step 300 to vary the current 254 that is passed through coil 100. This creates a desired application of various frequencies of PEMF to the desired part of the subject's body. This begins at step 304 when the frequency of the electrical current 254 applied by control unit 104 to coil 100 is set at a value determined by the treatment method selected in step 300.

During step 306 the coil 100 remains energized by an oscillating electrical current for a period of time determined by the selected method of treatment. This oscillating electrical current 254 generates a pulsed electromagnetic field 256 to treat the desired body part. After the desired period of time elapses, the control unit 104 determines at step 308 if the selected treatment method requires additional frequencies of PEMF be applied to the subject's body. If so, at step 310 the control unit 104 modifies the oscillating electrical current 254 to the next desired frequency and then continues to energize the coil 100 using that current 256 for a desired time period.

The time duration at step 306 and the increments between frequencies applied at step 310 may vary in length and amount between treatment methods and even for different frequencies within one treatment method. In some embodiments of the inventive methods, the increments may be so small that the PEMF approximates a continuously variable frequency of PEMF, while in other embodiments the increments may be substantial so that the PEMF varies in clearly discrete stages during treatment. In some embodiments, the frequency increments are 0.5 Hz and 1 Hz increments. In some embodiments the time increment is 15 seconds.

Once the final frequency of electrical current in the selected treatment has been applied to the coil 100, and control unit 100 determines at step 308 that no further steps are required for the treatment plan, it may be set at step 312 to automatically repeat the treatment method, or to end treatment and end the electrical current 254 to coil 100.

Figure 4:
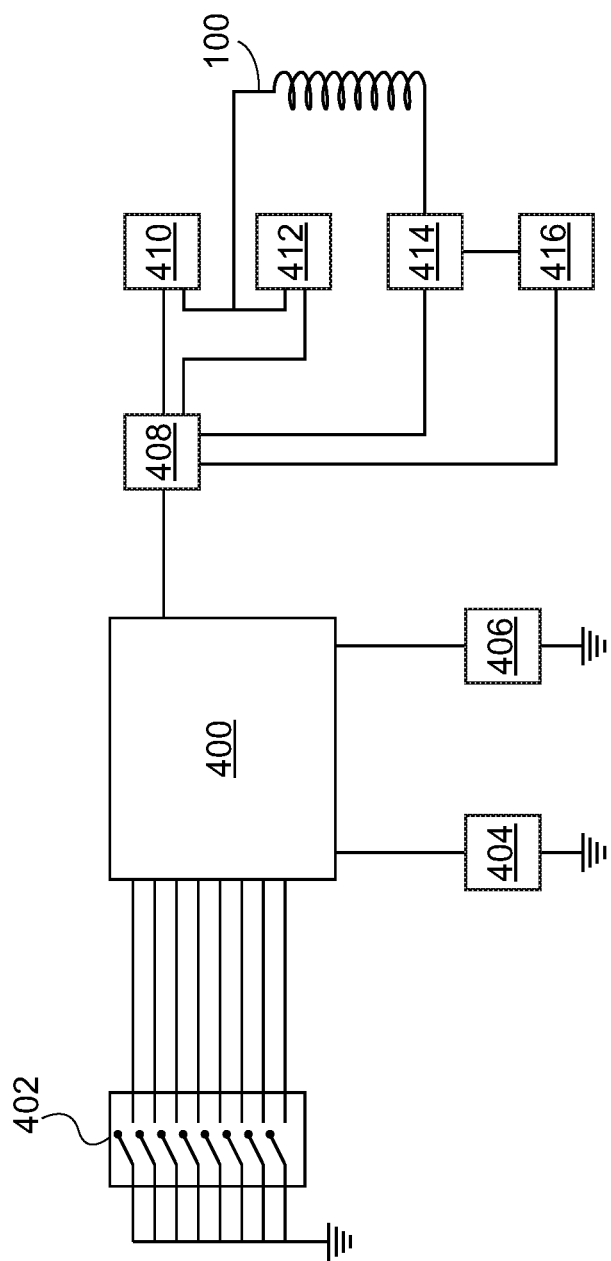
FIG. 4 is a schematic depiction of an embodiment of the PEMF device.

Referring now to FIG. 4, an electrical schematic diagram for an embodiment of the control unit 104 is depicted. The exact electrical components shown on the diagram or used in an embodiment are not limiting of the invention, as many other combination of electrical components may be created to provide the inventive method of PEMF therapy described in this application. In some embodiments of the inventive device, all or portions of the functions of the control unit 104 may be performed by a general purpose computer executing software designed to perform all or a portion of the functions of the control unit 104. Similarly a mobile device such as a mobile phone, tablet, or other personal electronic device may provide all or a portion of the functions of the control unit 104. In some embodiments, a control unit 104 with reduced capability may work in coordination with a general purpose computer, mobile device, or other personal electronic device to provide the functions described in this application as part of the control unit 104. For example, a tablet device may a user interface for a user to select and initiate a certain treatment methodology, and the tablet device may connect wirelessly to a control unit 104 and provide the user input to the control unit 104. The control unit 104 may then consist of electronics capable of receiving that user input and causing PEMF to be applied to the coil 100 according to the received user input.

In the depicted embodiment of the control unit 104, the electrical components of the control unit include a programmable microcontroller 400 having a central processing unit/processor core, memory, and programmable input/output terminals. The memory provided on the microcontroller 400 includes program memory to store program code for operating the microcontroller to operate the system to provide the PEMF treatments to a patient, and working memory for use during execution of the program by the processor core.

The depicted embodiment of the control unit 104 also includes jumpers and switches 402 to allow user input to select a desired PEMF therapy. In this embodiment, the program code operating on the microcontroller provides a desired therapy based on the settings of the jumpers and switches. The microcontroller also generates signals to control lights such as LED 404 and LED 406 shown on the schematic diagram to provide feedback to a user of the device. In other embodiments, the switches 402 may be replaced with a graphical user interface.

In the depicted embodiment, the microcontroller generates a desired variable PEMF signal. An array of transistors or other similar electrical amplifiers amplifies the signal to a desired level of current and voltage and drives the desire signal to the coil 100. In the depicted embodiment, transistor array 408 is used to control power transistors 410, 412, 414, and 416. The power transistors are connected to coil 100 to generate the desired pulsed magnetic field.

Methods of Using an Embodiment of the Device

A method of utilizing an embodiment of the device, comprises the following steps: (i) plug the connector 300 of cord 102 from the coil 100 into a port 204 marked COIL on the control unit; (ii) plug the cord 108 from the power supply/transformer 106 into the port 200 marked POWER on the control unit; (iii) provide power to the transformer 106 by plugging it into an electrical outlet. In the described embodiment, as the control unit 100 initiates operation the POWER light 202 will blink red several times then turn steady green.

In the depicted embodiment, the COIL light 206 will blink at the same frequency as the electrical signal currently running through the coil 100, indicating the unit 104 is working properly. In that embodiment, the light 206 will appear to be on continuously when the frequency of the electrical signal approaches 30 Hz and above. In this embodiment, every two minutes the coil light 206 will alternate from Green to Red and back indicating the direction of the electrical signal, and thus the orientation of the magnetic field, is reversing to prevent the body from acclimating to the PEMF.

In other embodiments of the inventive device, the control unit may be provided with displays of information regarding the current frequency or other information as may be desired, without departing from the spirit of the invention. Although no ON-OFF switch is provided in the depicted embodiment, others may be provided with such a switch.

In one embodiment the control unit 104 will continuously sweep the desired frequency range of the 7 lowest Schumann resonance frequencies plus and minus 2 Hz as long as power is applied. The 7 lowest Schumann resonance frequencies are a range of frequencies running from substantially 5.83 Hz thru 56.83 Hz. In other embodiments of the device, the control unit 104 may run a set number of cycles for each resonance frequency, or use a different range of frequencies, or may allow a user to select a frequency range, all within the scope of the current invention.

A small ⅜" neodymium magnet (or other similar magnet) may be utilized to check the coil 100 for proper operation. A user may place the magnet in an open hand and hold it directly on the coil 100, causing a vibration of the magnet corresponding to the current frequency of the electrical signal if all is working properly.

The PEMF frequency is substantially at the target frequency if it is within the range of variability produced by the electronics used in the control unit to generate the oscillating electrical current in the loop. Depending on the specific electronics utilized, the frequency actually generated by the coil may vary slightly from the resonance frequencies without departing from the scope of the claimed invention.

Treatment Methods

A wide variety of methods of treating a patient using PEMF may be performed using the device. A user may place the coil over an area of pain to target the therapy to that area. As an example of some coil placements, the patient may lay on their back or sit with the coil on their chest or behind or above the head, sit with the coil behind the back or beneath the buttocks, around an arm, shoulder, elbow, wrist, leg, knee, ankle, foot, or next to another joint of concern.

One embodiment of an inventive PEMF treatment consists of a frequency sweep from 2 Hz below the fundamental Schumann harmonic resonance to 2 Hz above the seventh harmonic of the Schumann resonance. In one embodiment of this treatment, the sweep frequency starts at 5.83 Hz and increases 1 Hz every 15 seconds thru 56.83 Hz. In this embodiment, a full sweep completes every 12 minutes and 45 seconds and may be configured to run continuously, returning to the low frequency immediately, or sweeping back through the frequency range to the low frequency end.

Other treatment methods may be utilized, and control unit 104 or a computer interface to control unit 104 may be used to alter the operation of the coil 100 accordingly. In the depicted embodiment, an 8 position DIP Switch 402 is provided to allow selection of alternative treatments. In the depicted embodiment, the frequency sweep described above will execute when all 8 DIP switches are in the OFF position. With respect to the DIP switches in the control unit 104 shown in the depicted embodiment, ON refers to a switch in the closed position, and OFF refers to a switch in the open position.

It may be desired to select one or more of the Schumann resonance harmonics for targeted treatment for a specific group of Chakras. To run a treatment targeted to any single Schumann resonance harmonic or a or combination thereof using the depicted embodiment of the control unit 104, Switch 8 is set to the OFF position, and the switches for the desired Schumann resonance harmonics are set to ON. For example, to run Schumann resonance harmonics 1, 2, 3, 5, and 6, the switches 1, 2, 3, 5, and 6 are set to ON and the remaining switches are set to OFF. With these settings the control unit 104 will generate PEMF signals through the coil for frequencies 4.83 Hz through 27.49 Hz and 35.15 Hz through 50.98 Hz.

The 7 Chakra frequencies (corresponding to the Schumann resonance harmonics) are: 7.83 Hz, 15.66 Hz, 23.49 Hz, 31.32 Hz, 39.15 Hz, 46.98 Hz, and 54.81 Hz. In the depicted embodiment of the control unit 104, when an individual Chakra frequency is selected using one of the switches, the sweep of the frequency will be a range substantially from −3 Hz to +4 Hz from the selected Chakra frequency. For example, Chakra 1 will run from approximately 4.83 Hz through 11.83 Hz, Chakra 2 will run from approximately 12.66 Hz through 19.66 Hz, etc.

It may be desired to target a single frequency without sweeping across multiple frequencies. In the depicted embodiment, the single frequency mode may be activated by setting switches 7 and 8 to the ON position. In some embodiments of the device, switches 1 through 6 may be used to select a frequency in the following manner (weighted in binary encoding), Switch 1=1 Hz, Switch 2=2 Hz, Switch 3=4 Hz, Switch 4=8 Hz, Switch 5=16 Hz, Switch 6=32 Hz. By setting a combination of switches to the ON position a specific desired frequency may be selected by adding the switch settings 1 thru 6 together to determine the coil frequency.

For example, to run 10 Hz PEMF to the coil using the depicted embodiment, a user sets Switches 7 and 8 to ON to select single frequency mode, and sets Switches 2 and 4 to the ON position (2 Hz+8 Hz=10 Hz) to select the desired frequency. Similarly, to run 20 Hz a user may set Switch 5 (16 Hz) and Switch 3 (4 Hz) (16 Hz+4 Hz=20 Hz) to the ON position. Similarly, Switches 1, 3, and 5 cause control unit 104 to generate PEMF at 21 Hz. In this embodiment of the device, a range of frequencies from 1 Hz to 63 Hz, in 1 Hz increments, may be selected by a user. If only DIP Switches 7 and 8 are set to ON, while Switches 1 through 6 are in the OFF position, the unit defaults to 0.5 Hz.

In the depicted embodiment, if Switch 8 is set to ON and Switch 7 is set to OFF other preprogrammed treatments may be selected using Switches 1 through 6, with binary weighting. The bump is the increase in frequency every 15 seconds. The following sweeps are selected using Switches 1 through 6 (with Sw 8 ON and Sw 7 OFF).

| Switch Settings | Treatment |
| --- | --- |
| Sw 1 through 6 OFF | 6.83 Hz to 8.83 Hz 4 times then, .5 Hz through 32 Hz, bump = 1 Hz |
| Sw 1 ON | 6.83 Hz to 8.83 Hz 4 times then, .5 Hz through 32 Hz, bump = .5 Hz |
| Sw 2 ON | Schumann Sweep 6.83 Hz through 8.83 Hz, bump = .5 Hz |
| Sw 1, Sw 2 ON | Delta Sweep 1 Hz through 4 Hz, bump = .5 Hz |
| Sw 3 On | Theta Sweep 4 Hz through 8 Hz, bump = .5 Hz |
| Sw 1, Sw 3 ON | Alpha Sweep 8 Hz through 12 Hz, bump = .5 Hz |
| Sw 2, Sw 3 ON | Beta Sweep 12 Hz through 32 Hz, bump = .5 Hz |
| Sw 1, Sw 2, Sw 3 ON | Delta + Theta Sweep 1 Hz through 8 Hz, , bump = .5 Hz |
| Sw 4 ON | Delta + Theta + Alpha Sweep 1 Hz through 12 Hz, bump = .5 Hz |

The following frequency hopping treatments are selected using Switches 1 through 6 (with Sw 8 ON and Sw 7 OFF). In these treatments, no frequency sweep is generated, but the control unit 104 generates PEMF at the selected frequencies for a period of time, such as 15 seconds, before hopping to the next frequency.

| Switch Settings | Treatment |
| --- | --- |
| Sw 1, Sw 6 ON | Schumann Hop (7.83, 15.66, 23.49, 31.32, 39.15, 46.98, and 54.81 Hz) |
| Sw 2, Sw 6 ON | Geomagnetic Hop (5.90, 11.79, 17.69, 23.58, 29.48, 35.37, 39.15, 41.27, 47.16, and 53.06 Hz) |
| Sw 1, Sw 2, Sw 6 ON | Schumann/Geomagnetic (all of the above from lowest to highest) |

In other embodiments of the PEMF device, the controller 400 may be programmed differently to assign different functions to the switches. In other embodiments, the switches of this embodiment may be replaced with a graphical user interface on a computing device such as a computer, laptop, mobile device, or a dedicated control unit with graphical capabilities.

Changes may be made in the above methods, devices and structures without departing from the scope hereof. Many different arrangements of the various components depicted, as well as components not shown, are possible without departing from the spirit and scope of the present invention. Embodiments of the present invention have been described with the intent to be illustrative and exemplary of the invention, rather than restrictive or limiting of the scope thereof. Alternative embodiments will become apparent to those skilled in the art that do not depart from its scope. Specific structural and functional details disclosed herein are not to be interpreted as limiting, but merely as a representative basis for teaching one of skill in the art to employ the present invention in any appropriately detailed structure. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A method of treating a patient with a pulsed electromagnetic field generated using an electrically conductive coil, the method comprising the steps of:

providing a control unit comprising: a microcontroller having a central processing unit, said microcontroller having memory, said microcontroller having a programmable input terminal, said microcontroller having a programmable output terminal, said microcontroller is electrically connected to a first light emitting diode and a second light emitting diode, said microcontroller generates signals to the first light emitting diode and the second light emitting diode, said microcontroller is electrically connected to an array of transistors, said array of transistors are in electrical communication with a plurality of control power transistors, said microcontroller is electrically connected to an 8-position dual in-line package switch; and, said control unit is electrically connected to a power source;

providing an electrically conductive coil, said electrically conductive coil having a first end and a second end, said first end of said electrically conductive coil and said second end of said electrically conductive coil are electrically connected to a cord, said cord having an end with a connector, said connector of said cord is electrically connected to said control unit, whereby, said electrically conductive coil is electrically connected to said plurality of control power transistors;

positioning said electrically conductive coil within proximity of a head of a patient;

said control unit generating an oscillating electrical current, whereby, energizing said electrically conductive coil with said oscillating electrical current having a range of approximately 5.83 Hz to approximately 56.83 Hz, whereby, inducing increased amplitude of neural oscillations in a gamma frequency band of approximately 30 Hz to 150 Hz, whereby, sufficiently generating a pulsed electromagnetic field configured to impinge on a brain of said patient; and, altering the frequency of said oscillating electrical current to vary the frequency of the pulsed electromagnetic field.

2. The method of claim 1, further comprising, the step of altering said frequency of said oscillating electrical current to a value that is substantially equal to a target frequency selected from the group of frequencies consisting of 33.83 Hz, 40.33 Hz, and 46.83 Hz.

3. The method of claim 2, further comprising, periodically and sequentially varying said frequency of said oscillating electrical current to a plurality of target frequencies selected from said group of frequencies.

4. The method of claim 2, further comprising, the step of incrementally varying said frequency of said oscillating electrical current in a range extending from 3 Hz lower than said target frequency to 4 Hz higher than said target frequency.

5. The method of claim 4, wherein said frequency is incrementally varied by 0.5 Hz or 1 Hz.

6. The method of claim 5, wherein said frequency is incrementally varied every 15 seconds.

7. The method of claim 2, further comprising, incrementally varying said frequency of the oscillating electrical current from a start frequency that is lower than said target frequency to an end frequency that is higher than said target frequency.

8. The method of claim 7, wherein said start frequency is 3 Hz lower than said target frequency and said end frequency is 4 Hz higher than said target frequency.

9. The method of claim 7, further comprising, repeating the step of incrementally varying for a second target frequency selected from said group of frequencies.

10. The method of claim 7, further comprising, repeating the step of incrementally varying for each of said target frequency in said group of frequencies.

11. The method of claim 10, wherein said target frequency is incrementally varied by 1 Hz every 15 seconds.

12. The method of claim 1, further comprising, the step of altering said frequency of said oscillating electrical current to a value that is selected from the group consisting of 31.32 Hz, 39.15 Hz, 46.98 Hz, and 54.81 Hz.

13. The method of claim 1, further comprising, incrementally varying said frequency of said oscillating electrical current from a first frequency substantially equal to 2 Hz lower than 7.83 Hz to a second frequency substantially equal to 2 Hz higher than 54.81 Hz.

14. The method of claim 13, further comprising, incrementally varying said frequency of said oscillating electrical current from said second frequency to said first frequency.

15. The method of claim 1, further comprising, placing said electrically conductive coil adjacent to said head of said patient in a halo position.

16. The method of claim 1, further comprising, the step of running a sweep frequency starting at 5.83 Hz and increasing 1 Hz every 15 seconds up to 52.83 Hz.

17. A method for treating a patient with an electrically-conductive coil, the method comprising the steps of:

providing a control unit comprising: a microcontroller having a central processing unit, said microcontroller having memory, said microcontroller having a programmable input terminal, said microcontroller having a programmable output terminal, said microcontroller is electrically connected to a first light emitting diode and a second light emitting diode, said microcontroller generates signals to the first light emitting diode and the second light emitting diode, said microcontroller is electrically connected to an array of transistors, said array of transistors are in electrical communication with a plurality of control power transistors, said microcontroller is electrically connected to an 8-position dual in-line package switch; and, said control unit is electrically connected to a power source;

providing an electrically conductive coil, said electrically conductive coil having a first end and a second end, said first end of said electrically conductive coil and said second end of said electrically conductive coil are electrically connected to a cord, said cord having an end with a connector, said connector of said cord is electrically connected to said control unit, whereby, said electrically conductive coil is electrically connected to said plurality of control power transistors;

positioning a head of the patient inside said electrically conductive coil;

said control unit generating an oscillating electrical current, whereby, said oscillating electrical current is applied to said electrically conductive coil, said oscillating electrical current having at least one Chakra frequency selected from the group of Chakra frequencies consisting of 7.83 Hz, 15.66 Hz, 23.49 Hz, 31.32 Hz, 39.15 Hz, 46.98 Hz, and 54.81 Hz, to generate an oscillating magnetic field;

selecting said at least one Chakra frequency using weighted binary encoding, whereby, switch 1 of said 8-position dual in-line package switch is equal to 1 Hz, switch 2 of said 8-position dual in-line package switch is equal to 2 Hz, switch 3 of said 8-position dual in-line package switch is equal to 4 Hz, switch 4 of said 8-position dual in-line package switch is equal to 8 Hz, switch 5 of said 8-position dual in-line package switch is equal to 16 Hz, switch 6 of said 8-position dual in-line package switch is equal to 32 Hz;

orienting at least one switch of said 8-position dual in-line package switch in an ON position to cause said control unit to generate a desired frequency; and, applying said oscillating magnetic field to a brain of said patient to induce an increased amplitude of brain waves of said patient in the range of 30 Hz to 150 Hz.

18. The method of claim 17, wherein the polarity of said oscillating magnetic field varies with the direction of said oscillating electrical current.

\* \* \* \* \*